Figure 1:
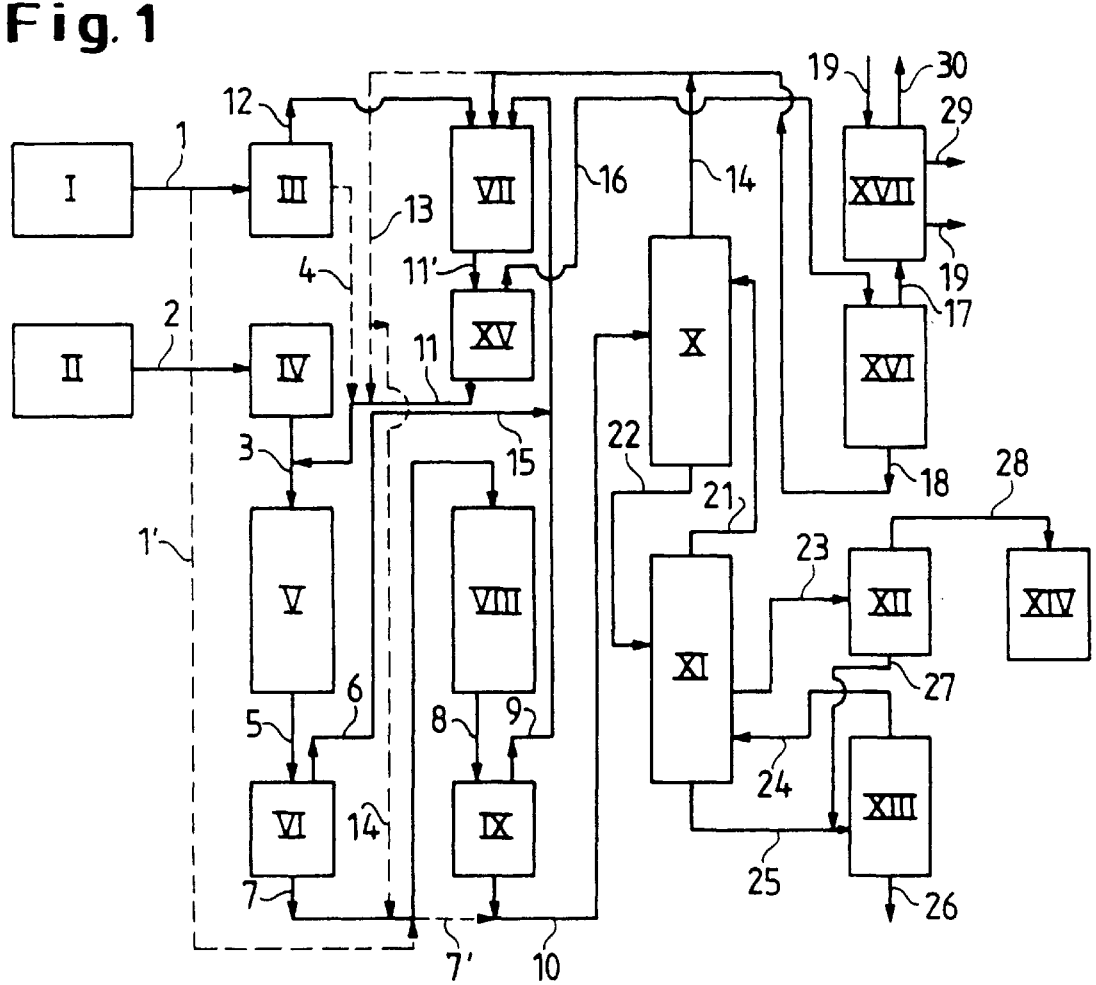

United States Patent [19]
Ooms et al.

[11] Patent Number: 5,831,111
[45] Date of Patent: Nov. 3, 1998

[54] PROCESS FOR THE CONTINUOUS PRODUCTION OF ARYL CARBONATES

[75] Inventors: Pieter Ooms, Krefeld, Germany; Eric Bischof, Baytown, Tex.; Hans-Josef Buysch, Krefeld, Germany; Steffen Kühling, Meerbusch, Germany; Gottfried Zaby, Leverkusen, Germany; Wolfgang Jakob, Moers, Germany; Jürgen Dahmer, Krefeld, Germany; Norbert Schön, Würzburg, Germany

[73] Assignee: Bayer AG, Leverkusen, Germany

[21] Appl. No.: 850,474

[22] Filed: May 5, 1997

[30] Foreign Application Priority Data

May 13, 1996 [DE] Germany ............... 196 19 224.2

[51] Int. Cl.⁶ ................................................ C07C 68/02
[52] U.S. Cl. .................. 558/274; 546/153; 546/174; 546/301; 558/271
[58] Field of Search ................... 558/271, 274; 546/153, 174, 301

[56] References Cited

U.S. PATENT DOCUMENTS

| | | | |
|---|---|---|---|
| 2,362,865 | 11/1944 | Tryon et al. | 558/274 |
| 2,837,555 | 6/1958 | Lee | 558/274 |
| 3,234,263 | 2/1966 | Kurkjy et al. | 558/274 |
| 5,136,077 | 8/1992 | Rand | 558/274 |
| 5,239,105 | 8/1993 | Pews et al. | 558/274 |
| 5,252,771 | 10/1993 | Harley et al. | 558/274 |
| 5,473,094 | 12/1995 | Ooms et al. | 558/270 |
| 5,478,961 | 12/1995 | Ooms et al. | 558/270 |
| 5,524,942 | 6/1996 | Fleming | 292/73 |

FOREIGN PATENT DOCUMENTS

| | | |
|---|---|---|
| 0 483 632 | 5/1992 | European Pat. Off. . |
| 0 516 355 | 12/1992 | European Pat. Off. . |
| 0 635 476 | 1/1995 | European Pat. Off. . |
| 0 635 477 | 1/1995 | European Pat. Off. . |
| 0 645 364 | 3/1995 | European Pat. Off. . |
| 0 691 326 | 1/1996 | European Pat. Off. . |
| 0 722 930 | 7/1996 | European Pat. Off. . |
| 91/06526 | 5/1991 | WIPO . |

OTHER PUBLICATIONS

Orbit Abstract of EP 0 483 632 (May 6, 1992).
Orbit Abstract EP 0 635 476 (Jan. 25, 1995).
Orbit Abstract of EP 0 635 477 (Jan. 25, 1995).
Orbit Abstract EP 0 645 364 (Mar. 29, 1995).
Orbit Abstract of EP 0 691 326 (Jan. 10, 1996).
Orbit Abstract of EP 0 722 930 (Jul. 24, 1996).

Primary Examiner—Michael G. Ambrose
Attorney, Agent, or Firm—Connolly & Hutz

[57] ABSTRACT

The present invention relates to a process for the continuous production of carbonates having aromatic ester groups by reacting aromatic hydroxy compounds with phosgene in the gas phase in the presence of heterogeneous catalysts.

20 Claims, 1 Drawing Sheet

| I | phenol storage tank | X, XI, XII, XIII | distillation column |
| II | phosgene storage tank | XIV | product tank (DPC) |
| III, IV | heat exchanger | XVI | cold trap |
| V, VII, VIII | reactor | XVII | HCl absorber |
| VI, IX, XV | condensation unit/degasser | | |

PROCESS FOR THE CONTINUOUS PRODUCTION OF ARYL CARBONATES

This invention relates to a process for the continuous production of carbonates having aromatic ester groups by reacting aromatic hydroxy compounds with phosgene in the gas phase in the presence of heterogeneous catalysts.

It is known that aryl carbonates may be obtained by phase interface phosgenation (Schotten-Baumann reaction) of aromatic hydroxy compounds. In this reaction, the use of solvents and sodium hydroxide solution has a disadvantageous effect as the aqueous alkali solution may bring about partial saponification of phosgene or chloroformic acid esters, large quantities of common salt are produced as a secondary product and the solvent has to be recovered.

Proposals for processes without solvents are made, for example, in U.S. Pat. Nos. 2,837,555; 3,234,263; 2,362,865. However, soluble catalysts are used, the separation of which from the products is elaborate.

Consequently it seems convenient to use heterogenous, insoluble catalysts, which substantially facilitate working up the reaction mixture. Proposals have also been made in this connection. EP-A-516 355 thus primarily recommends aluminium trifluoride, which is optionally applied onto supports such as aluminosilicates. However, the handling of fluorine or hydrofluoric acid makes synthesising aluminium fluoride very complicated and costly. WO 91/06526 describes metal salts on porous supports as catalysts for fully continuous phosgenation of phenol in the gas and liquid phase. Partial condensation of diphenyl carbonate entails the risk of leaching the active catalyst constituents from the supports and thus of deactivation.

Further disadvantages include unsatisfactory conversion rates even in the presence of a large excess of phenol or phosgene, while in the event of an excess of phosgene considerable fractions of the unwanted chloroformic acid phenyl ester are obtained, which would result in complicated working up. No continuous industrial process for the production of diaryl carbonates by phosgenating aromatic hydroxy compounds in the gas phase in the presence of uniform, heterogeneous catalysts has thus hitherto been proposed.

Such a process has now been found. It is characterised in that 1) a gaseous mixture heated to 180° C. to 500° C. of an aromatic hydroxy compound and optionally the chloroformic acid ester thereof, optionally diluted with an inert gas or with the vapour of an inert solvent, on the one hand, and phosgene heated to 20° C. to 500° C., on the other, are introduced into a cylindrical reaction chamber without moving parts, filled with heterogeneous catalyst and heated to 180° C. to 500° C. and allowed to react therein, whereby the reaction temperature rises by at most 150° C. above the inlet temperature of the reaction mixture, 2) the gas mixture leaving the reactor is partially condensed, the waste gas is introduced together with a gaseous or molten stream of the aromatic hydroxy compound, which optionally contains some chloroformic acid ester, into an additional waste gas reactor filled with heterogeneous catalyst and is allowed to react therein in such a manner that phosgene and optionally chloroformic acid ester are removed from the exit gas stream, 3) the condensed and degassed reaction product leaving the reactor is either passed directly for working up or introduced into a second reactor, in which any remaining chloroformic acid ester is reacted further over a heterogeneous catalyst, with aromatic hydroxy compound still present or introduced to yield diaryl carbonate, 4) the product leaving the second reactor is again degassed and this waste gas is introduced into the waste gas reactor referred to in 2) together with the molten or gaseous aromatic hydroxy compound, 5) the degassed product from the second reactor is introduced into a distillation column, the aromatic hydroxy compound and any traces of chloroformic acid ester optionally still present are distilled off as a top product and reintroduced into the waste gas reactor or into the first reactor, 6) the bottom product of this first column is introduced into a second distillation column, in which any traces of low-boiling components optionally still present are removed from the diaryl carbonate as a top product and returned into the upper part of the first column, 7) pure diaryl carbonate, optionally with traces of high-boiling components, is discharged from the gas space of the second column, 8) this product is introduced into a third column and by separating the residual quantities of high-boiling components as the bottom product, pure diaryl carbonate is obtained as overhead product, 9) the combined bottom products from the second and third columns are passed into a fourth distillation unit, diaryl carbonate is distilled off as the top product, returned to the second column and the high-boiling components are removed from the bottom of the fourth distillation unit.

Aromatic hydroxy compounds for of the process according to the invention are those of the formula ArOH, in which Ar means phenyl, naphthyl, anthryl, phenanthryl, indanyl, tetrahydronaphthyl or the residue of a 5- or 6-membered aromatic heterocycle having 1 or 2 heteroatoms selected from the group comprising N, O and S, wherein these isocyclic and heterocyclic residues may be substituted by one or more substituents such as linear or branched $C_1-C_4$ alkyl, $C_1-C_4$ alkenyl, $C_1-C_4$ alkoxy groups, phenyl residues or nitrile and halogen functions and wherein the heterocyclic residues may furthermore be fused to a benzene ring.

Examples of aromatic hydroxy compounds according to the invention are: phenol, o-, m- and p-cresol, o-, m- and p-isopropylphenol, the corresponding halo- or alkoxyphenols, such as p-chlorophenol or p-methoxyphenol, together with monohydroxy compounds of naphthalene, anthracene and phenanthrene, as well as hydroxypyridine and hydroxyquinolines. Substituted phenols are preferably used, with phenol itself being particularly preferably used.

The aromatic hydroxy compounds and the chloroformic acid esters thereof are vaporised before performance of the process according to the invention and continuously heated to a temperature within the temperature range from 180° to 500° C., preferably from 200° to 400° C., particularly preferably of 220° to 350° C. The previously heated aromatic hydroxy compounds may be used in the process according to the invention as they are or diluted with inert gas or with the vapour of an inert solvent. Thorough mixing of the aromatic hydroxy compound vapour with the inert gas may be achieved, for example, by vaporising the aromatic hydroxy compound in a stream of an inert gas or the vapour of an inert solvent. The preferred inert gas is nitrogen. Suitable inert solvents, the vapour of which may also be used to dilute the aromatic hydroxy compounds, are, for example, chlorobenzene, o-dichlorobenzene, xylene, chloronaphthalene, decahydronaphthalene or mixtures thereof.

The quantity of the inert gas or solvent vapour optionally used as diluent is not critical.

Suitable catalysts for the process according to the invention are known, for example from EP-A 483 632, EP-A 635 476, U.S. Pat. No. 5,478,961, EP-A 635 477, U.S. Pat. No. 5,473,094, EP-A 645,364, U.S. Pat. No. 5,524,942, EP-A 691 326, EP-A 722 930, EP-A 516 355, U.S. Pat. No. 5,239,105 and U.S. Pat. No. 5,136,077.

The educts phosgene and hydroxy compound are used in molar ratios of 1:0.5 to 1:8, preferably of 1:1.5 to 1:5, particularly preferably of 1:2 to 1:4. In this case, the stoichiometric ratio is 1:2.

The catalysts are generally used as granular material, pellets, extrudates, rods, spheres, high-surface area mouldings such as hollow extrudates in the form of Raschig rings, hollow cylinders, stars, wagon wheels or as broken pieces. The diameter and length of these particles range from 0.5 to 10 mm. They are arranged in the reactor in the form of a simple packing.

Before the process according to the invention is performed, the stream of phosgene is heated to a temperature within the range from 20° to 500° C., preferably from 100° to 400° C., particularly preferably from 220° to 350° C.

In order to perform the reaction according to the invention, the pre-heated streams of the aromatic hydroxy compound, or of the mixture of aromatic hydroxy compound and inert gas or vapour of an inert solvent, on the one hand, and the phosgene, on the other, are continuously introduced into a cylindrical reaction chamber and mixed together therein.

Reactors suitable for the process according to the invention are known to the person skilled in the art. Examples are tubular reactors without moving parts within the reactor, optionally having cooling or heating jackets, which contain the catalyst as a packing, or rack reactors, in which the catalyst is distributed as a uniform layer on two or more superposed trays.

The tubular reactors generally consist of steel, glass, alloy or enamelled steel and are of a length sufficient to ensure the virtually complete reaction of the aromatic hydroxy compound with the phosgene under the processing conditions. The gas streams are generally introduced into one end of the tubular reactor, wherein this introduction may, for example, proceed through nozzles accommodated at one end of the tubular reactor or through a combination of a nozzle and an annular gap between the nozzle and the mixing tube or through a distributor plate.

The reaction of phosgene and aromatic hydroxy compound is performed at temperatures of approximately 180° to 500° C., preferably of 200° to 400° C., particularly preferably of 220° to 350° C.

Pressure ranges from 0.1 to 10 bar, preferably from 0.2 to 7 bar, particularly preferably from 0.3 to 6 bar.

Flow through the reactor may be ensured by establishing an appropriate pressure differential between the product feed lines into the reaction chamber, on the one hand, and the outlet from the reaction chamber on the other. In general, the pressure in the feed lines into the reaction chamber is 200 to 3000 mbar and 150 to 2000 mbar at the outlet from the reaction chamber. The essential point in this connection is merely to maintain a pressure differential in order to ensure flow through the reaction chamber. The gaseous mixture leaving the reaction chamber is generally cooled and sent for working up or partially condensed and introduced into a second reactor.

Partial condensation may optionally be performed using an inert solvent, the temperature of which is selected such that the diaryl carbonate and a solvent optionally used as a diluent condense or dissolve in the inert solvent, while excess phosgene, hydrogen chloride and the inert gas optionally used as a diluent pass through the condensation stage or the inert solvent in gaseous form. Examples of selective condensation are the passage of the gas mixture through the inert solvent or spraying the solvent (atomised solvent) into the stream of gas.

Suitable solvents which may be used for selective condensation are, for example, chlorobenzene, o-dichlorobenzene, xylene, chloronaphthalene, decahydronaphthalene or mixtures thereof, preferably dichlorobenzene and particularly preferably the aromatic hydroxy compound itself.

However, cooling or partial condensation may also in principle be performed with a heat exchanger.

The waste gas remaining after the partial condensation is passed co- or counter-currently through a reactor filled with heterogeneous catalyst, together with a molten or gaseous stream of the hydroxy compound, which may also contain chloroformic acid ester in quantities of <50 wt. %, preferably of <30 wt. %, particularly preferably of <10 wt. %, wherein the remaining phosgene and any relatively small quantities of chloroformic acid ester possibly still entrained are removed from the waste gas stream. The molten mixture leaving the waste gas post-reactor is adjusted to the desired molar ratio by the addition of optionally further hydroxy compound, vaporised, heated to the desired temperature and introduced into the reactor.

The gas stream leaving the top of the waste gas post-reactor once the reaction mixture has been degassed substantially consists of hydrogen chloride. Any phosgene possibly still present may be hydrolysed with a little water using known methods in an activated carbon tower. The quantity of the hydroxy compound still present in the stream of hydrogen chloride, the quantity being determined by the compound's vapour pressure at the temperature prevailing in the degassing apparatus, is removed by freezing in a cold trap and may be returned to the reactor. Any possible residual amount is driven off by azeotropic distillation as an aqueous mixture in the subsequent adiabatic absorption of the hydrogen chloride in water and, once recovered, may be introduced into the reactor or alternatively used for other purposes, such as the production of phenolic resins.

The residual quantities of phosgene still present in the hydrogen chloride may, after the adiabatic absorption with water, where they are driven off with the azeotropic mixture of the hydroxy compound and water, also advantageously be introduced into the activated carbon tower with the traces of inert gas originating from the educt streams and hydrolysed therein.

Once the reaction mixture has been partially condensed, an initial crude product is obtained, which generally predominantly consists of diaryl carbonate and aromatic hydroxy compound and which still contains certain quantities of chloroformic acid ester, which generally amount to <50 wt. %, preferably <30 wt. %, very particularly preferably <15 wt. %.

This mixture may be passed directly for working up by distillation and divided into streams consisting of chloroformic acid ester and hydroxy compound, a diaryl carbonate and small quantities of high-boiling components. However, for simplicity's sake and to ensure that distillation is performed more economically, a more suitable reaction mixture contains no or only small quantities of chloroformic acid ester.

The initial molten crude product obtained after the partial condensation is thus advantageously passed into a second reactor containing heterogeneous catalyst and the chloroformic acid ester still present is reacted therein in the liquid phase with the hydroxy compound still present in or added to the mixture. Pressure may here be maintained within relatively narrow limits of 0.1 to 6, preferably from 0.2 to 4 bar. Temperature is from 120° to 250° C., preferably from 140° to 250° C., particularly preferably from 160° to 230° C.

Reactor loading, measured in kilograms of educt mixture per liter of catalyst volume per hour is dependent upon the reaction temperature, the activity of the catalysts and the desired conversion rate. Loading is 0.01 to 20, preferably from 0.02 to 10, particularly preferably from 0.03 to 4, most preferably from 0.04 to 3 kg/l -h.

The mixture leaving the second reactor is degassed and the waste gas stream is also passed into the waste gas second reactor. The degassed mixture, which contains only small quantities (<3, preferably <2, particularly preferably <1 wt. %) of chloroformic acid ester is freed in a first distillation column of excess hydroxy compound and chloroformic acid ester or optionally used solvent, which are discharged as a top product and, as required, passed into the reactor, second reactor or into the waste gas reactor and further reacted.

The mixture discharged from the bottom of this column is separated in a second column into residual low-boiling components, which are returned into the upper part of the first column, pure diaryl carbonate, which is discharged laterally from the vapour stream of this second column, and a mixture of diaryl carbonate and high-boiling components, which leaves the column as the bottom product.

By being introduced into a third column, the diaryl carbonate, which is discharged as the top product from this third column, is separated from traces of high-boiling components (bottom product).

The combined bottom products from the second and third columns are separated in a fourth distillation apparatus, which is operated continuously or discontinuously, into a bottom product containing high-boiling components and diaryl carbonate, which is passed into the lower part of the second column and is further purified therein.

The comparatively small quantities of bottom product of <3, preferably of <2, particularly preferably of <1% of the reaction product are expediently incinerated or used for phenolic resin production.

EXAMPLE

Continuous production of diphenyl carbonate by gas phase phosgenation of phenol in the presence of γ-aluminium oxide The apparatus used to perform the process according to the invention and the material streams occurring are schematically represented in FIG. 1.

Together with phenol 14 discharged from the top of distillation column X and phenol 18 returned from the cold trap XVI, 54.0 parts by weight/h of phenol 12 are apportioned from a heated tank I via heat exchanger III (170° C.) under standard pressure into the top of an waste gas post-reactor VII heated to 170° C. and filled with 45 parts by volume of γ-aluminium oxide. The waste gas stream 15 (weight ratio of phenol/phosgene/hydrogen chloride/carbon dioxide 1.7/52.9/44.8/0.6) originating from the condensation apparatus VI and degassing apparatus IX is introduced in concurrent flow with the phenol into the reactor VII.

The product 11' leaving the base of the reactor, which contains phenol, chloroformic acid ester, diphenyl carbonate and secondary products in a ratio of 82.0/1.35/16.6/0.05 is separated by means of degasser XV into waste gas 16 (weight ratio of phenol, phosgene, hydrogen chloride and carbon dioxide 4.0/66.3/29.5/0.2) and bottom product 11 (weight ratio of phenol, chloroformic acid phenyl ester, diphenyl carbonate and secondary products 81.9/1.4/16.7/0.05).

40.6 parts by weight/h of phosgene 3 preheated by means of heat exchanger IV (280° C.) are introduced in concurrent flow with 11 preheated to 280° C. into a reactor V heated to 280° C. and filled with 45 parts by volume of γ-aluminium oxide.

The product 5 leaving the base of the reactor, which contains phenol, chloroformic acid phenyl ester, diphenyl carbonate and secondary products in a ratio of 34.1/4.3/61.3/0.3, is separated by means of condensation apparatus VI into waste gas 6 (weight ratio of phenol, phosgene, hydrogen chloride and carbon dioxide 0.9/54.8/43.7/0.6) and bottom product 7 (weight ratio of phenol, chloroformic acid phenyl ester, diphenyl carbonate and secondary products 33.9/4.3/61.5/0.3).

The chloroformic acid phenyl ester present in the bottom product 7 is converted to diphenylcarbonate at 180° C. by subsequent reaction with phenol present (possibly after the addition of additional phenol (1' or 14')) in a second reactor VIII, which is also filled with γ-aluminium oxide (45 parts by volume).

The product 8 discharged at the base of the reactor (weight ratio of phenol, diphenyl carbonate and secondary products 31.7/68.0/0.3) is separated by means of degasser IX into waste gas 9 (phenol/hydrogen chloride) and bottom product 10 (weight ratio of phenol, diphenyl carbonate and secondary products 31.5/68.2/0.3).

Waste gas streams 6 and 9 are combined to give 15 and passed into waste gas reactor VII in concurrent flow with phenol (12, 14 and 18) as already mentioned above.

The waste gas 16 leaving the top of the degasser XV is passed into a cold trap XVI, in which the phenol 18 present (0.70 parts by weight/h) is removed and returned into the waste gas reactor VII.

The waste gas 17 leaving the cold trap XVI is passed into a hydrogen chloride absorption unit XVII.

By introducing 124.4 parts by weight/h of an 18% hydrochloric acid 19, 145.7 parts by weight/h of a 30% hydrochloric acid 20 are obtained, which may be supplied for electrolysis. The chlorine obtained from electrolysis may be reused for the production of phosgene.

Traces of entrained phenol may be removed as an azeotropic mixture with water 29.

A destruction unit (activated carbon towers with water) is connected to destroy any phosgene still present in the waste gas 30.

Bottom product 10 is introduced into a first distillation column X and separated at approximately 80° C./12 torr into 28.1 parts by weight/h of phenol and bottom product 22 (weight ratio of phenol, diphenyl carbonate and secondary products 0.31/99.3/0.4).

Bottom product 22 is passed into a second distillation column XI, in which the phenol 21 still present (0.2 parts by weight/h) is removed as a top product and reintroduced into the upper part of the first column X.

61.3 parts by weight/h of product 23 (weight ratio of diphenyl carbonate, secondary products 99.9/0.1) are obtained by lateral discharge from the gas space of the second column XI, which is separated in a third distillation column XII into a top product 28 (61.3 parts by weight/h of diphenyl carbonate) and bottom product 27, which flows into column XIII.

The product 25 (weight ratio of diphenyl carbonate/ secondary products 90.6/9.4) discharged at the base of the distillation column XI is separated together with 27 in a fourth distillation column XIII at 170° C./12 torr into a top product 24 (1.8 parts by weight/h of diphenyl carbonate), which is returned to the lower part of the second column XI, and bottom product 26 (high-boiling secondary products).

EXAMPLE 2

Performing the process according to the invention as described in Example 1, but without the waste gas reactor and at 330° C. with the introduction of 71.9 parts by weight/h of phenol 4 via heat exchanger III and introduction of 37.1 parts by weight/h of phosgene 3 preheated by means of heat exchanger IV into reactor V, gives rise at constant selectivity to 26.1 parts by weight/h of diphenyl carbonate.

The following further variations to the described procedure, depending on educt and product composition, catalyst loadings and temperature may be mentioned:

a) apportionment of phenol 4 directly into the reactor V instead of via the waste gas reactor VII at the start of the process.

b) addition of phenol (1' or 14') as additional reaction partner for the post-reaction in the case where of relatively high concentrations of chloroformic acid phenyl ester are present.

c) operation without post-reaction in reactor VIII, whereby the chloroformic acid phenyl ester still present is distilled off with phenol in the first distillation column X as a low-boiling component 14 and introduced into waste gas reactor VII, or, where the process is operated without an waste gas post-reactor, is returned to the first reactor V (13).

d) operation with phosgene scrubbing instead of waste gas reactor VII and degasser XV, whereby waste gas stream 15 is passed countercurrently to molten phenol (1, 14 or 18) from the bottom of a countercurrent apparatus.

We claim:

1. Process for the continuous production of diaryl carbonates by reacting phosgene with aromatic hydroxy compounds in the presence of heterogeneous catalysts, characterised in that 1) a gaseous mixture heated to 180° C. to 500° C. of an aromatic hydroxy compound and optionally the chloroformic acid ester thereof, optionally diluted with an inert gas or with the vapour of an inert solvent, on the one hand, and phosgene heated to 20° C. to 500° C., on the other, are introduced into a first reactor consisting essentially of a reaction chamber without moving parts, filled with heterogeneous catalyst and heated to 180° C. to 500° C. and allowed to react therein as a reaction mixture, whereby the reaction temperature rises by at most 150° C. above the inlet temperature of the reaction mixture, 2) the product leaving the first reactor is partially condensed in a first degassing unit, waste gas from the first degassing unit is introduced together with a gaseous or molten stream of the aromatic hydroxy compound, which optionally contains some chloroformic acid ester, into a first waste gas reactor filled with heterogeneous catalyst and is allowed to react therein in such a manner that phosgene and optionally chloroformic acid ester are removed from the waste gas stream, 3) degassed reaction product leaving the first degassing unit is either passed directly for working up or introduced into a second reactor, in which any remaining chloroformic acid ester is reacted further, over a heterogeneous catalyst, with aromatic hydroxy compound still present or introduced to yield diaryl carbonate, 4) the product leaving the second reactor is again degassed in a second degassing unit and waste gas from the second degassing unit is introduced into the first waste gas reactor referred to in 2) together with the molten or gaseous aromatic hydroxy compound referred to in 2), 5) the degassed product from the second degassing unit is introduced into a first distillation column, wherein the aromatic hydroxy compound and any traces of chloroformic acid ester optionally still present are distilled off as a top product and reintroduced into the first waste gas reactor or into the first reactor, 6) the bottom product of this first column is introduced into a second distillation column, in which any traces of low-boiling components optionally still present are removed from the diaryl carbonate as a top product and returned into the upper part of the first column, 7) diaryl carbonate, optionally with traces of high-boiling components, is discharged from the gas space of the second column, 8) this product is introduced into a third column and by separating the residual quantities of high-boiling components as the bottom product, pure diaryl carbonate is obtained as overhead product, 9) the combined bottom products from the second and third columns are passed into a fourth distillation unit, diaryl carbonate is distilled off as the top product, returned to the second column and the high-boiling components are removed from the bottom of the fourth distillation unit.

2. The process of claim 1, wherein in step 1) the aromatic hydroxy compound and optionally the chloroformic acid ester thereof that are introduced into the first reactor are at a temperature of 200° to 400° C.

3. The process of claim 1, wherein in step 1) the aromatic hydroxy compound and optionally the chloroformic acid ester thereof that are introduced into the first reactor are at a temperature of 220° to 350° C.

4. The process of claim 1, wherein the aromatic hydroxy compound and optionally the chloroformic acid ester thereof are diluted with an inert gas or with the vapour of an inert solvent.

5. The process of claim 4, wherein the inert gas is nitrogen.

6. The process of claim 4, wherein the inert solvent is at least one substance selected from the group consisting of chlorobenzene, o-dichlorobenzene, xylene, chloronaphthalene and decahydronaphthalene.

7. The process of claim 1, wherein the molar ratio of the phosgene to the aromatic hydroxy compound is from 1:0.5 to 1:8.

8. The process of claim 1, wherein the molar ratio of the phosgene to the aromatic hydroxy compound is from 1:1.5 to 1:5.

9. The process of claim 1, wherein the molar ratio of the phosgene to the aromatic hydroxy compound is from 1:2 to 1:4.

10. The process of claim 1, wherein the phosgene is heated to 220° to 350° C.

11. The process of claim 1, wherein the pressure in the first reactor is from 0.1 to 10 bar.

12. The process of claim 1, wherein the pressure in the first reactor is from 0.3 to 6 bar.

13. The process of claim 1, wherein the pressure in the second reactor is from 0.1 to 6 bar.

14. The process of claim 1, wherein the pressure in the second reactor is from 0.2 to 4 bar.

15. The process of claim 1, wherein the temperature in the second reactor is from 120° to 250° C.

16. The process of claim 1, wherein the temperature in the second reactor is from 140° to 250° C.

17. The process of claim 1, wherein the temperature in the second reactor is from 160° to 230° C.

18. The process of claim 1, wherein the aromatic hydroxy compound is a compound of the formula ArOH, in which Ar means phenyl, naphthyl, anthryl, phenanthryl, indanyl, tetrahydronaphthyl or the residue of a 5- or 6-membered aromatic heterocycle having 1 or 2 heteroatoms selected from the group consisting of N, O and S, further wherein Ar may be substituted by one or more substituents.

19. The process of claim 1, wherein the aromatic hydroxy compound is selected from the group consisting of phenol, o-cresol, m-cresol, p-cresol, o-isopropylphenol, m-isopropylphenol, p-isopropylphenol, p-chlorophenol, p-methoxyphenol, monohydroxy compounds of naphthalene, monohydroxy compounds of anthracene, monohydroxy compounds of phenanthrene, hydroxypyridine and hydroxyquinoline.

20. The process of claim 1, wherein the aromatic hydroxy compound is phenol or a substituted phenol.

* * * * *